US010285664B2

United States Patent
Song et al.

(10) Patent No.: US 10,285,664 B2
(45) Date of Patent: May 14, 2019

(54) X-RAY IMAGING APPARATUS, CONTROL METHOD FOR THE SAME, AND X-RAY DETECTOR

(71) Applicant: Samsung Electronics Co., Ltd, Gyeonggi-do (KR)

(72) Inventors: Sang Ha Song, Gyeonggi-do (KR); Jae Hyun Lim, Gyeonggi-do (KR)

(73) Assignee: Samsung Electronics Co., Ltd., Suwon-si (KR)

( * ) Notice: Subject to any disclaimer, the term of this patent is extended or adjusted under 35 U.S.C. 154(b) by 221 days.

(21) Appl. No.: 15/389,370

(22) Filed: Dec. 22, 2016

(65) Prior Publication Data

US 2017/0172536 A1   Jun. 22, 2017

(30) Foreign Application Priority Data

Dec. 22, 2015 (KR) .................. 10-2015-0183701

(51) Int. Cl.
*A61B 6/00* (2006.01)
*A61B 6/06* (2006.01)

(52) U.S. Cl.
CPC ............. *A61B 6/587* (2013.01); *A61B 6/06* (2013.01); *A61B 6/4417* (2013.01); *A61B 6/461* (2013.01);
(Continued)

(58) Field of Classification Search
CPC ......... A61B 6/587; A61B 6/06; A61B 6/4417; A61B 6/461; A61B 6/547; A61B 6/548;
(Continued)

(56) References Cited

U.S. PATENT DOCUMENTS 6,447,163 B1 * 9/2002 Bani-Hashemi ......... A61B 6/08
378/205
2004/0125921 A1   7/2004 Allouche et al.
(Continued)

FOREIGN PATENT DOCUMENTS

DE   102014210897 A1 * 12/2015 ........... A61B 6/4411
DE   102014210897 A1   12/2015
(Continued)

OTHER PUBLICATIONS

European Patent Office, "Supplementary European Search Report," Application No. EP 16879331.3, dated Oct. 12, 2018, 9 pages.

*Primary Examiner* — Courtney D Thomas

(57) ABSTRACT

Disclosed herein are an X-ray imaging apparatus for photographing a marker provided in an X-ray detector with a camera to acquire information about the distance between the X-ray detector and an X-ray source or information about the pose of the X-ray detector at low cost The X-ray imaging apparatus may include an X-ray source that generates X-rays and irradiates the X-rays. A photographing device installed in the X-ray source photographs a marker image. A controller outputs, when a marker of a plurality of markers constituting a multi-marker array formed in a surface of an X-ray detector is not detected from the marker image, a notice informing that no marker is detected. The controller detects a single marker from another marker image photographed after the notice informing that the marker is not detected is outputted.

20 Claims, 19 Drawing Sheets

(52) U.S. Cl.
CPC .............. *A61B 6/547* (2013.01); *A61B 6/548* (2013.01); *A61B 6/583* (2013.01); *A61B 6/588* (2013.01); *A61B 6/4283* (2013.01); *A61B 6/4405* (2013.01); *A61B 6/4464* (2013.01)

(58) Field of Classification Search
CPC ....... A61B 6/583; A61B 6/588; A61B 6/4283; A61B 6/4405; A61B 6/4464; G01N 23/046; G01N 2223/419
USPC ........................................................ 378/205
See application file for complete search history.

(56) References Cited

U.S. PATENT DOCUMENTS

| | | |
|---|---|---|
| 2011/0013752 A1 | 1/2011 | Takahashi |
| 2011/0254922 A1 | 10/2011 | Schaerer et al. |

FOREIGN PATENT DOCUMENTS

| | | | |
|---|---|---|---|
| JP | 2011092612 A | * | 5/2011 |
| JP | 2011092612 A | | 5/2011 |
| JP | 2012005508 A | * | 1/2012 |
| JP | 2012005508 A | | 1/2012 |
| JP | 2013111216 A | * | 6/2013 |
| JP | 2013111216 A | | 6/2013 |
| WO | 2014036034 A1 | | 3/2014 |

* cited by examiner

X-RAY IMAGING APPARATUS, CONTROL METHOD FOR THE SAME, AND X-RAY DETECTOR

CROSS-REFERENCE TO RELATED APPLICATION(S) AND CLAIM OF PRIORITY

The present application is related to and claims the benefit of Korean Patent Application No. 10-2015-0183701, filed on Dec. 22, 2015 in the Korean Intellectual Property Office, the disclosure of which is incorporated herein by reference.

TECHNICAL FIELD

Embodiments of the present disclosure relate to an X-ray imaging apparatus of acquiring information about the distance between an X-ray detector and an X-ray source using a marker, a method of controlling the X-ray imaging apparatus, and the X-ray detector.

BACKGROUND

An X-ray imaging apparatus is equipment for irradiating X-rays on an object and analyzing the X-rays transmitted through the object to thereby show the internal structure of the object. The X-ray imaging apparatus can image the internal structure of an object using a fact that different tissues in the object have different attenuation coefficients obtained by digitizing degrees to which the respective tissues transmit X-rays.

Meanwhile, in order to set X-ray irradiation conditions, information about Source to Object Distance (SOD) representing the distance between an X-ray source and an object or Source to Image receptor Distance (SID) representing the distance between the X-ray source and an X-ray detector is needed.

Also, in order to automatically align the poses and locations of the X-ray source and the X-ray detector, information about the pose and location of the X-ray detector is needed in addition to information about the distance between the X-ray source and the X-ray detector.

SUMMARY

To address the above-discussed deficiencies, it is a primary object to provide an X-ray imaging apparatus of photographing a marker provided in an X-ray detector with a camera to acquire information about the distance between the X-ray detector and an X-ray source and information about the pose of the X-ray detector at low cost, a method of controlling the X-ray imaging apparatus, and the X-ray detector.

Additional aspects of the disclosure will be set forth in part in the description which follows and, in part, will be obvious from the description, or may be learned by practice of the disclosure.

In accordance with an aspect of an exemplary embodiment, the X-ray imaging apparatus may comprise an X-ray source configured to generate X-rays, and to irradiate the X-rays a photographing device installed in the X-ray source, and configured to photograph a marker image; and a controller configured to output, if no marker of a plurality of markers constituting a multi-marker array formed in a surface of an X-ray detector is detected from the marker image, a notice informing that no marker is detected, and to detect a single marker from another marker image photographed after the notice informing that no marker is detected is output.

If at least one marker of the plurality of markers is detected, the controller may be configured to determine a location of the detected marker, and determines Source to Image receptor Distance (SID) based on a location relationship between the detected marker and the center of the X-ray detector.

If the single marker is detected, the controller may be configured to determine a location of the detected single marker, and determines SID based on a location relationship between the detected single marker and the center of the X-ray detector.

The apparatus may further comprise a storage configured to store features of the plurality of markers constituting the multi-marker array, and features of the single marker.

The photographing device may photograph a moving image, and the controller may be configured to detect motion from the moving image, and if the controller fails to detect motion from the moving image for a predetermined time period, the controller may be configured to control the photographing device to photograph the marker image.

The single marker may be displayed on a display of a mobile device, the X-ray imaging apparatus may further comprise a communicator configured to receive at least one of acceleration information and pose information of the mobile device from the mobile device.

The controller may be configured to detect motion of the mobile device based on at least one of the acceleration information and the pose information of the mobile device, and if the controller fails to detect motion of the mobile device for a predetermined time period, the controller may be configured to transmit a control signal for causing the photographing device to photograph the other marker image to the photographing device.

A collimator marker may be formed in the X-ray source, and the communicator is configured to receive a photographed image of the collimator marker from the mobile device.

The controller may be configured to determine a location of the X-ray source based on the photographed image of the collimator marker, and determine a location of the X-ray detector based on the marker image.

If at least one marker of the plurality of markers is detected, or if the single marker is detected, the controller may be configured to determine a pose of the X-ray detector based on the detected marker.

The controller may be configured to align a pose of the X-ray source based on the pose of the X-ray detector.

The controller may be configured to determine a location of the X-ray detector based on a location of the detected marker, and align a location of the X-ray source based on the location of the X-ray detector.

The controller may be configured to determine a thickness of the object based on the SID, and sets an X-ray irradiation condition based on the thickness of the object.

In accordance with an aspect of another exemplary embodiment an X-ray detector may comprise an X-ray sensor configured to detect X-rays, and to generate an electrical signal corresponding to the detected X-rays; a case configured to accommodate the X-ray sensor; a multi-marker array including a plurality of markers formed in a front surface of the case to which the X-rays are incident; and a marker installation unit formed in one lateral surface of the case, wherein a single marker is attached to the marker installation unit.

The marker installation unit is configured such that the single marker is detachably attached to the marker installation unit.

The X-ray detector may further comprise a single marker attached to the marker installation unit in such a way as to be able to be folded and unfolded with respect to the marker installation unit, and the single marker is configured to be located on the rear surface of the X-ray detector when the single marker is folded, and located on one lateral surface of the X-ray detector when the single marker is unfolded.

The plurality of markers may be configured to have different features that are distinguished from each other, and the different features include at least ones of different colors and different patterns.

In accordance with an aspect of another exemplary embodiment, a method of controlling an X-ray imaging apparatus may comprise photographing a marker image at a camera installed in an X-ray source; outputting, if no marker of a plurality of markers constituting a multi-marker array formed in a surface of an X-ray detector is detected from the marker image, a notice informing that no marker is detected; and detecting a single marker from another marker image photographed after the notice informing that no marker is detected is output.

The method may further comprise: determining, if the single marker is detected, a location of the single marker; and determining Source to Image receptor Distance (SID) based on a location relationship between the single marker and the center of the X-ray detector.

The photographing of the marker image may comprise: detecting motion from a moving image photographed by the camera; and capturing the marker image if no motion is detected from the moving image for a predetermined time period.

The single marker may be configured to be displayed on a display of a mobile device, the method may further comprise receiving at least one of acceleration information and pose information of the mobile device from the mobile device.

The photographing of the marker image may comprise: detecting motion of the mobile device based on at least one of the acceleration information and the pose information of the mobile device; and at the camera, capturing the other marker image if no motion of the mobile device is detected for a predetermined time period.

A collimator marker may be formed in the X-ray source, the method may further comprise receiving a photographed image of the collimator marker from the mobile device.

The method may further comprise: determining a location of the X-ray source based on the photographed image of the collimator marker; and determining a location of the X-ray detector based on the marker image.

Before undertaking the DETAILED DESCRIPTION below, it may be advantageous to set forth definitions of certain words and phrases used throughout this patent document: the terms "include" and "comprise," as well as derivatives thereof, mean inclusion without limitation; the term "or," is inclusive, meaning and/or; the phrases "associated with" and "associated therewith," as well as derivatives thereof, may mean to include, be included within, interconnect with, contain, be contained within, connect to or with, couple to or with, be communicable with, cooperate with, interleave, juxtapose, be proximate to, be bound to or with, have, have a property of, or the like; and the term "controller" means any device, system or part thereof that controls at least one operation, such a device may be implemented in hardware, firmware or software, or some combination of at least two of the same. It should be noted that the functionality associated with any particular controller may be centralized or distributed, whether locally or remotely. Definitions for certain words and phrases are provided throughout this patent document, those of ordinary skill in the art should understand that in many, if not most instances, such definitions apply to prior, as well as future uses of such defined words and phrases.

BRIEF DESCRIPTION OF THE DRAWINGS

For a more complete understanding of the present disclosure and its advantages, reference is now made to the following description taken in conjunction with the accompanying drawings, in which like reference numerals represent like parts.

DETAILED DESCRIPTION

FIGS. 1 through 18, discussed below, and the various embodiments used to describe the principles of the present disclosure in this patent document are by way of illustration only and should not be construed in any way to limit the scope of the disclosure. Those skilled in the art will understand that the principles of the present disclosure may be implemented in any suitably arranged imaging apparatus.

Hereinafter, embodiments of an X-ray imaging apparatus and a control method thereof according to an aspect will be described in detail with reference to the accompanying drawings.

Figure 1:
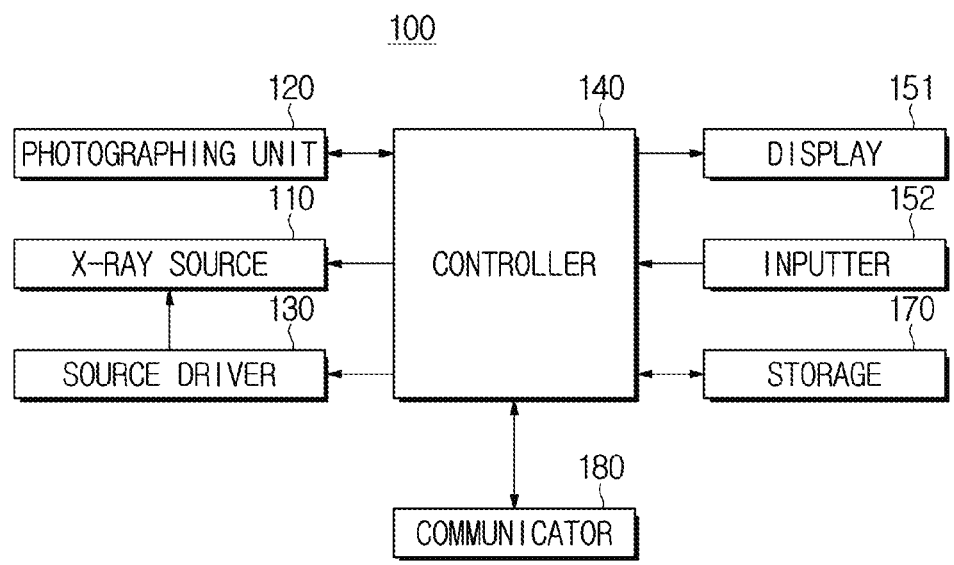
FIG. 1 illustrates a control block diagram of an X-ray imaging apparatus according to an embodiment of the present disclosure.
Figure 2:
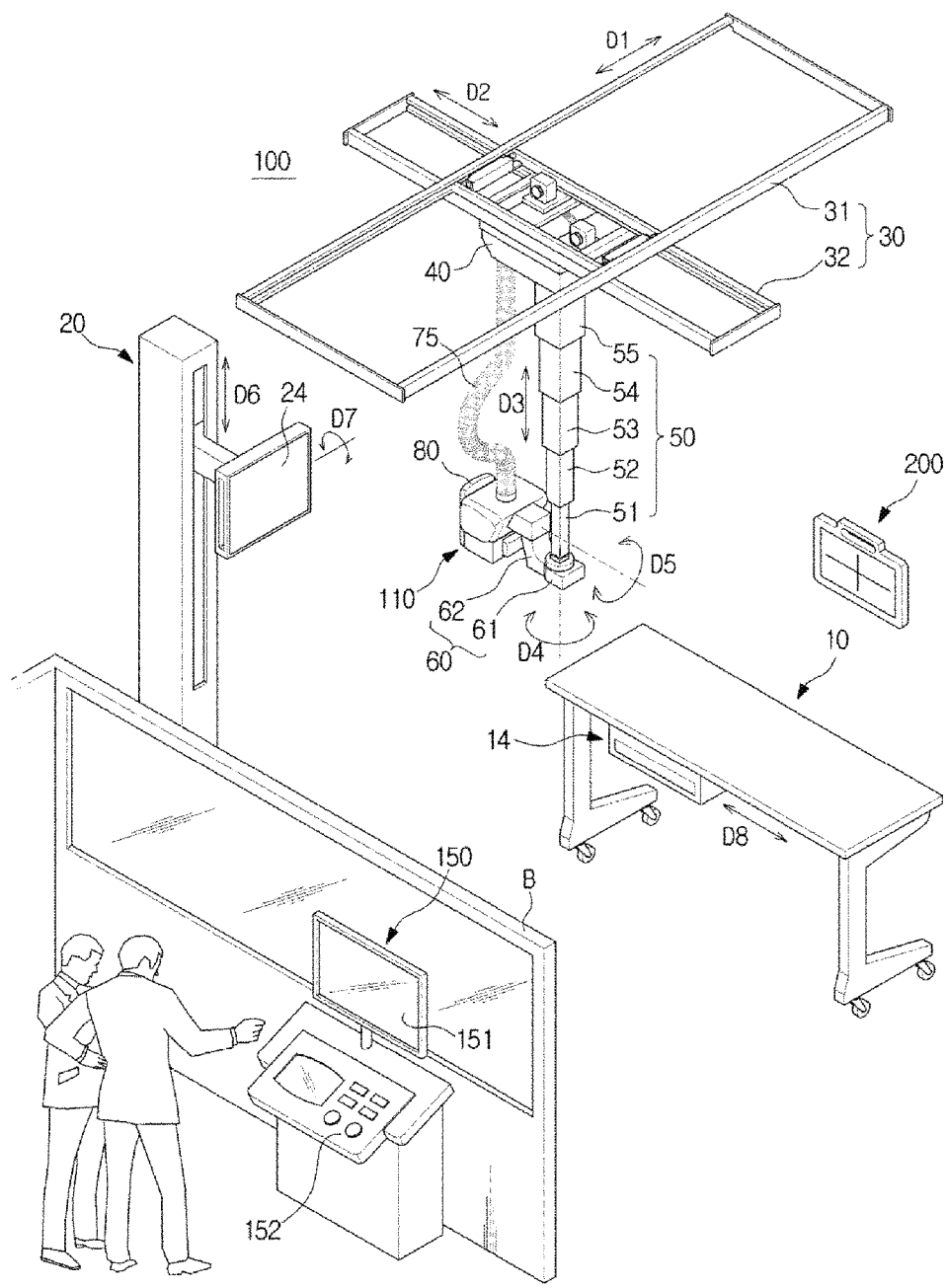
FIGS. 2 and 3 illustrate the outer appearance of an X-ray imaging apparatus according to an embodiment of the present disclosure.
Figure 3:
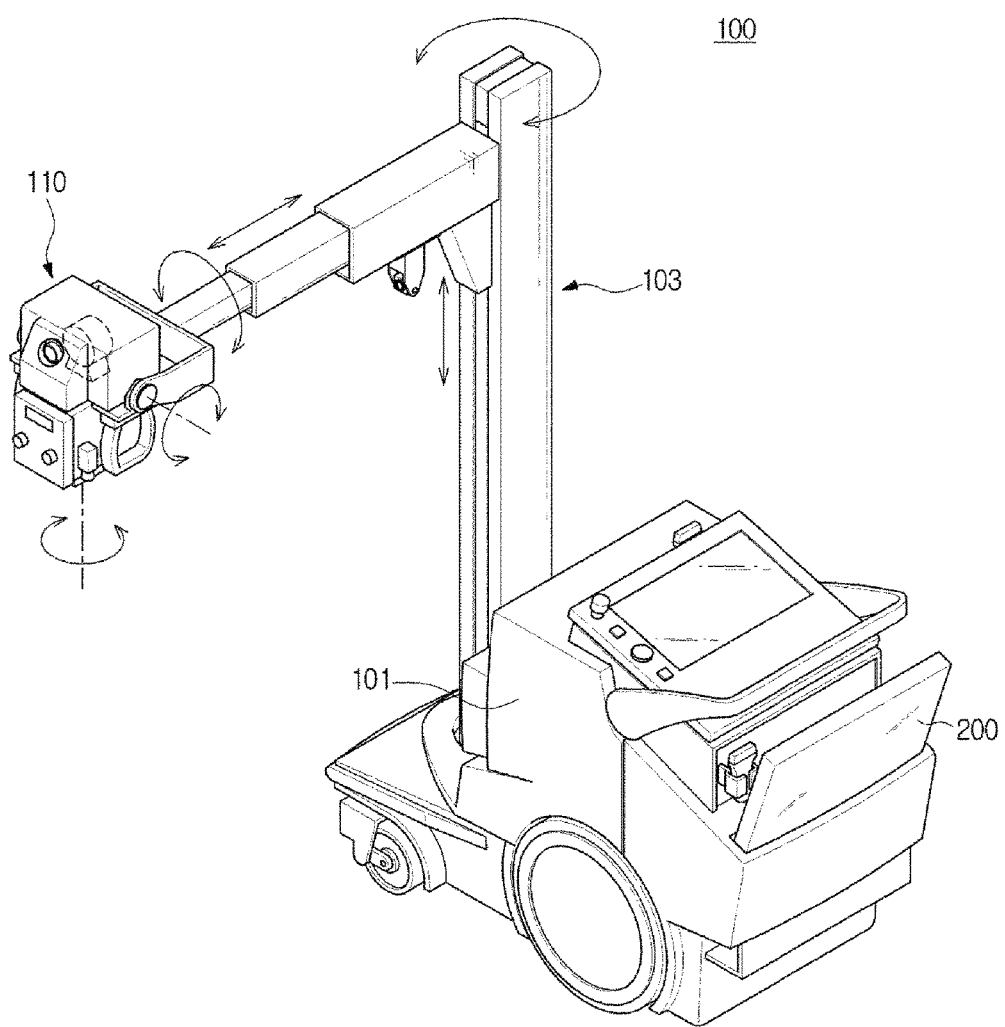

FIG. 1 illustrates a control block diagram of an X-ray imaging apparatus according to an embodiment of the present disclosure, and FIGS. 2 and 3 illustrate the outer appearance of an X-ray imaging apparatus according to an embodiment of the present disclosure.

Referring to FIG. 1, an X-ray imaging apparatus 100 according to an embodiment of the present disclosure may include: an X-ray source 110 configured to generate X-rays and to irradiate the X-rays onto an object; a photographing device 120 installed in the X-ray source 110 and configured to photograph a marker image; a source driver 130 configured to move the X-ray source 110; a controller 140 configured to analyze the marker image photographed by the photographing device 120 to determine a distance between an X-ray detector 200 (see FIG. 2) and the X-ray source 110; a display 151 configured to display a screen for providing a user with information about radiography or guiding the user to input a control command, an image photographed by the photographing device 120, or an X-ray image; an inputter 152 configured to receive a control command from the user; a storage 170 in which X-ray irradiation conditions are stored for the thickness of an object; and a communicator 180 configured to communicate with the X-ray detector 200 or other external devices to transmit/receive data to/from the X-ray detector 200 or the other external devices.

Hereinafter, operations of the individual components of the X-ray imaging apparatus 100 will be described in detail with reference to FIGS. 2 and 3 showing the outer appearance of the X-ray imaging apparatus 100.

FIG. 2 shows the outer appearance of a ceiling type X-ray imaging apparatus which is an embodiment of an X-ray imaging apparatus, wherein an X-ray source is connected to the ceiling of an examination room.

Referring to FIG. 2, a guide rail 30 may be mounted on the ceiling of an examination room where an X-ray imaging apparatus 100 is placed, and an X-ray source 110 may be connected to a moving carriage 40 moving along the guide rail 30 so that the X-ray source 110 can move to a location corresponding to an object.

The guide rail 30 may include a first guide rail 31 and a second guide rail 32 arranged to form a predetermined angle with respect to each other. For example, the first guide rail 31 may be orthogonal to the second guide rail 32.

The first guide rail 31 may be mounted on the ceiling of the examination room, and the second guide rail 32 may be disposed beneath the first guide rail 31 in such a way to be able to slide with respect to the first guide rail 31.

The moving carriage 40 may be disposed beneath the second guide rail 32 in such a way to be movable along the second guide rail 32. The moving carriage 40 may be movable in a first direction D1 together with the second guide rail 32, and movable in a second direction D2 along the second guide rail 32.

A post frame 50 may be connected to the lower portion of the moving carriage 40. The post frame 50 may include a plurality of posts 51, 52, 53, 54, and 55. The posts 51, 52, 53, 54, and 55 may connect to each other such that they can be folded with each other. The length of the post frame 50 fixed on the moving carriage 40 may increase or decrease in an elevation direction of the examination room, that is, in a third direction D3.

Since the X-ray source 110 is connected to the lower end of the post frame 50, the height of the X-ray source 110 from the floor may be controlled by increasing or decreasing the length of the post frame 50.

As described above, the X-ray source 110 is to irradiate X-rays on an object. The X-ray source 110 may include an X-ray tube to generate X-rays, and a collimator to adjust an irradiation area of the generated X-rays.

The X-ray source 110 may be connected to the moving carriage 40 through a connection pipe 75. In the inside of the connection pipe 75, various cables and wires may be installed to connect the X-ray source 110 to other devices, and a high voltage generated by a high voltage generator may be also supplied to the X-ray source 110 through the connection pipe 75.

The X-ray source 110 may photograph X-ray images of an object, whereas the photographing device 120 may be implemented as a camera, such as a Charge Coupled Device (CCD) camera and a Complementary Metal Oxide Semiconductor (CMOS) camera, to photograph moving images. Also, the photographing device 120 may photograph still images at short time intervals, or capture a still image at a specific time while photographing moving images. For example, the photographing device 120 may capture a still image at a specific time while photographing moving images to thereby photograph a marker image.

If a predetermined event occurs, the controller 140 may control the photographing device 120 to capture a still image. The predetermined event for capturing a still image may be a user's control command input through an inputter provided in a remote controller 300, a workstation 150, or a sub user interface 80, which will be described later.

The controller 140 may control the photographing device 120 to capture a marker image when a control command is received, when a predetermined time period elapses after a control command is received, or periodically for a predetermined time period from when a control command is received.

Alternatively, the controller 140 may analyze moving images photographed by the photographing device 120 in real time to detect motion, and if the controller 140 detects no motion for a predetermined time period, the controller 140 may determine that it is ready to perform radiography, and capture a marker image.

For example, the photographing device 120 (see FIG. 1) may be installed in the X-ray source 110, and more specifically, the photographing device 120 may be installed in the X-ray source 110 in a direction in which the X-ray source 110 irradiates X-rays. That is, the photographing device 120 may be installed to photograph images in a direction facing an object and the X-ray detector 200.

If the photographing device 120 is installed in the X-ray source 110, an offset between an area appearing in an X-ray image and the corresponding area appearing in an object image may become small so that a user can easily make settings related to the X-ray image while seeing the object image.

A revolute joint 60 may be disposed between the X-ray source 110 and the post frame 50. The revolute joint 60 may include a first revolute joint 61 connected to the lower post 51 of the post frame 50, and a second revolute joint 62 connected to the X-ray source 110.

The first revolute joint 61 may rotate in a fourth direction D4, and the second revolute joint 62 may rotate in a fifth direction D5. If the second revolute joint 62 rotates in the fifth direction D5, a tilt angle of the X-ray source 110 may be adjusted.

Also, the X-ray source 110 may be connected to the post frame 50 by the revolute joint 60 to linearly move in the first direction D1, the second direction D2, and the third direction D3.

The source driver 130 (see FIG. 1) may include a plurality of motors for linearly moving or rotating the X-ray source 110 in the first to fifth directions D1 to D5.

In one side of the X-ray source 110, a sub user interface 80 may be disposed to provide the user with information and to receive a control command from the user. Herein, the user may be a person who photographs an X-ray image of an object using the X-ray imaging apparatus 100, and the user may be a medical staff including a doctor, a radiologist, and a nurse. However, the user is not limited to a medical staff, and may be anyone using the X-ray imaging apparatus 100.

Although not shown in FIG. 2, the sub user interface 80 may include a display and an inputter. The user may use the display and the inputter to input a movement location of the X-ray source 110. The controller 140 may control the source driver 130 according to the user's input to linearly move the X-ray source 110 in the first direction D1, in the second direction D2, or in the third direction D3, or to rotate the X-ray source 110 in the fourth direction D4 or in the fifth direction D5. This is defined as an automatic move mode. In a manual move mode, the user may move the X-ray source 110 to a desired location.

Also, the user may input a control command for capturing a marker image through the inputter provided in the sub user interface 80, as described above.

The X-ray imaging apparatus 100 may further include a workstation 150 for controlling overall operations of the X-ray imaging apparatus 100. For example, the workstation 150 may be located in separate space partitioned by a baffle wall B from space where the X-ray source 110 is located.

The workstation 150 may include a display 151 to display X-ray images, a screen for guiding the user to input a control command, various setting information related to the X-ray imaging apparatus 100, etc., and an inputter 152 to receive various control commands related to radiography from the user.

The display 151 may be implemented as a Cathode Ray Tube (CRT), a Digital Light Processing (DLP) panel, a Plasma Display Panel (PDP), a Liquid Crystal Display (LCD) panel, an Electro Luminescence (EL) panel, an Electrophoretic Display (EPD) panel, an Electrochromic Display (ECD) panel, a Light Emitting Diode (LED) panel, or an Organic Light Emitting Diode (OLED) panel, although not limited to these.

The inputter 152 may be implemented as a keyboard, a mouse, a trackball, a jog shuttle, or a touch pad. If the inputter 152 is implemented as a touch pad and disposed on the front surface of the display 151, the inputter 152 may implement a touch screen together with the display 151.

A scanning table 10 on which an object can lie or sit for radiography may be provided adjacent to a movement range of the X-ray source 110.

The X-ray detector 200 may be installed in a detector installation unit 14 of the scanning table 10, or in a detector installation unit 24 of a scanning stand 20. However, radiography may be performed without installing the X-ray detector 200 in the scanning table 10 or the scanning stand 20, according to a patient's state or a part to be scanned. In this case, after the X-ray detector 200 is located behind a part of an object to be scanned, X-rays may be irradiated on the part to be scanned to perform radiography.

Meanwhile, the X-ray imaging apparatus 100 may be implemented as a mobile X-ray imaging apparatus as shown in FIG. 3. In the mobile X-ray imaging apparatus, since a main body 101 to which the X-ray source 110 is connected can freely move, an arm 103 connecting the X-ray source 110 to the main body 101 may also have a multi-degree of freedom so as to freely move the X-ray source 110.

When the X-ray imaging apparatus 100 is implemented as a mobile X-ray imaging apparatus, likewise, X-rays may be irradiated on a part to be scanned after the X-ray detector 200 is located behind the part to be scanned to perform radiography.

Meanwhile, an X-rays irradiation condition may be decided according to an object's characteristics, a scanning environment, etc. The X-ray irradiation condition may include at least one of a tub voltage, tube current, an exposure time, the kind and thickness of a filter, a target material of an anode, an exposure parameter such as a focal spot size, the angle or center position of a grid, and a scattering parameter such as Field Of View (FOV).

More specifically, when the X-ray irradiation condition is decided, the thickness of an object may be considered. For example, the controller 140 may acquire the thickness of an object by subtracting SOD from SID. In this case, in order to acquire the thickness of the object, information about SID and SOD is needed.

Also, in the automatic move mode of automatically aligning the location and pose of the X-ray source 110, information about the distance between the X-ray source 110 and the X-ray detector 200 and about the location and pose of the X-ray detector 200 may be needed in order to align the location and pose of the X-ray source 110 with respect to to the X-ray detector 200.

The X-ray imaging apparatus 100 according to an embodiment of the present disclosure may recognize a marker provided on or near the X-ray detector 200 to determine the distance between the X-ray source 110 and the X-ray detector 200 and the location and pose of the X-ray detector 200. Hereinafter, an embodiment will be described.

Figure 4:
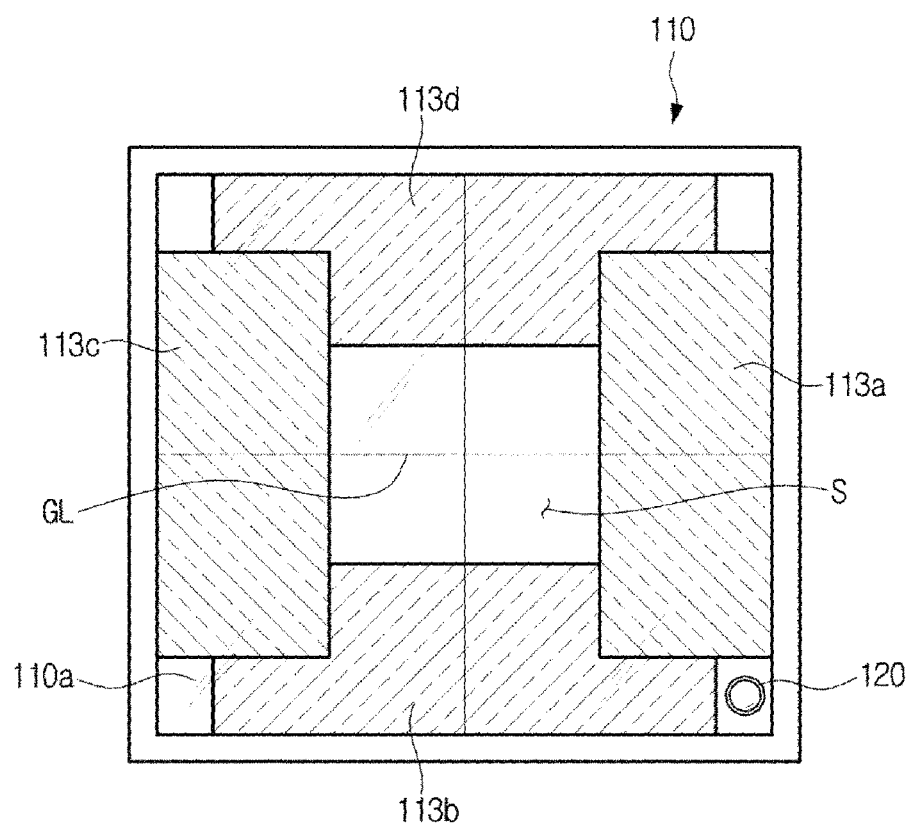
FIG. 4 illustrates an X-ray source in a direction in which X-rays are irradiated.

FIG. 4 illustrates an X-ray source in a direction in which X-rays are irradiated.

As described above, the X-ray source 110 may include the X-ray tube to generate X-rays, and the collimator to adjust an irradiation area of the generated X-rays. The collimator may be located in front of the X-ray tube, that is, in a direction in which X-rays are irradiated.

Referring to FIG. 4, the collimator 113 may include a plurality of movable blades 113a, 113b, 113c, and 113d, and the blades 113a, 113b, 113c, and 113d may be made of a material having a high bandgap to absorb X-rays. The blades 113a, 113b, 113c, and 113d may move to adjust an irradiation range of X-rays. More specifically, X-rays may be irradiated through a slot S formed by the blades 113a, 113b, 113c, and 113d.

The collimator 113 may further include a motor to provide a driving force to the respective blades 113a, 113b, 113c, and 113d. The plurality of blades 113a, 113b, 113c, and 113d may move independently. The controller 140 may calculate a movement amount of each of the blades 113a, 113b, 113c, and 113d so that X-rays can be irradiated on a predetermined irradiation area, and transmit a control signal for moving each of the blades 113a, 113b, 113c, and 113d by the calculated movement amount to the collimator 113.

The photographing device 120 may be installed adjacent to the collimator 113. A housing 110a may be disposed on the front surface of the collimator 113. The housing 110a may be made of a material, such as a transparent resin or glass, to minimize an influence on X-rays irradiated from the X-ray tube 111.

Also, in the housing 110a disposed on the front surface of the collimator 113, a cross-shaped guide line GL may be formed. If a light source installed in the X-ray source 110 emits light, a shadow of the guide line GL may appear on an X-ray irradiation area so that a user sees the shadow of the guide line GL to intuitively determine the location of the X-ray irradiation area.

The photographing device 120 may be installed in the X-ray source 110, as shown in FIG. 4, however, the installation location of the photographing device 120 is not limited to the X-ray source 110. That is, the photographing device 120 may be located outside the X-ray source 110, or disposed at any location at which it can photograph a marker image.

Figure 5A:
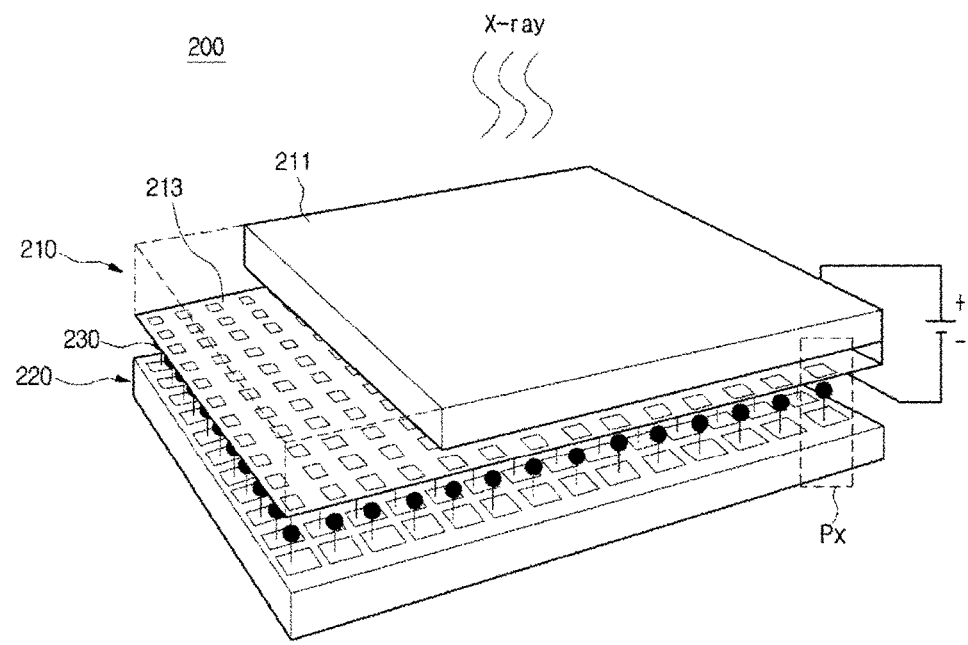
FIG. 5A illustrates the internal structure of an X-ray detector.
Figure 5B:
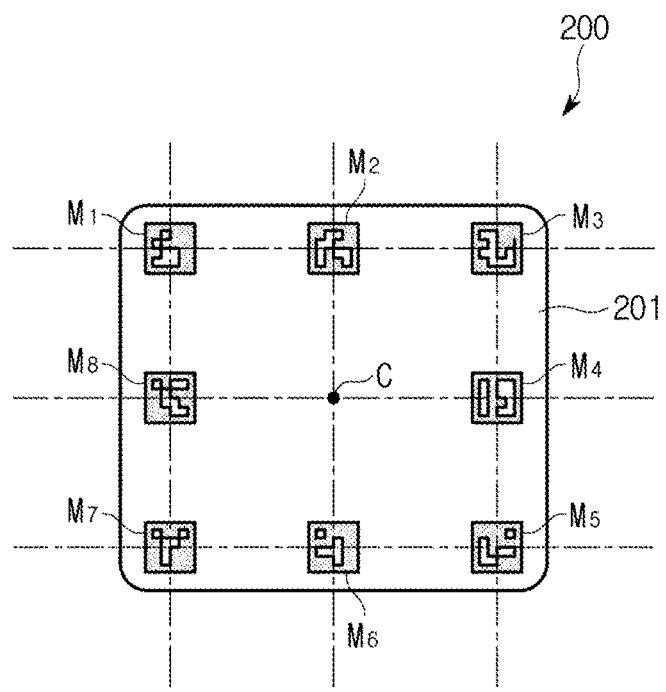
FIG. 5B illustrates an example of an X-ray detector on which a multi-marker array is disposed.
Figure 6:
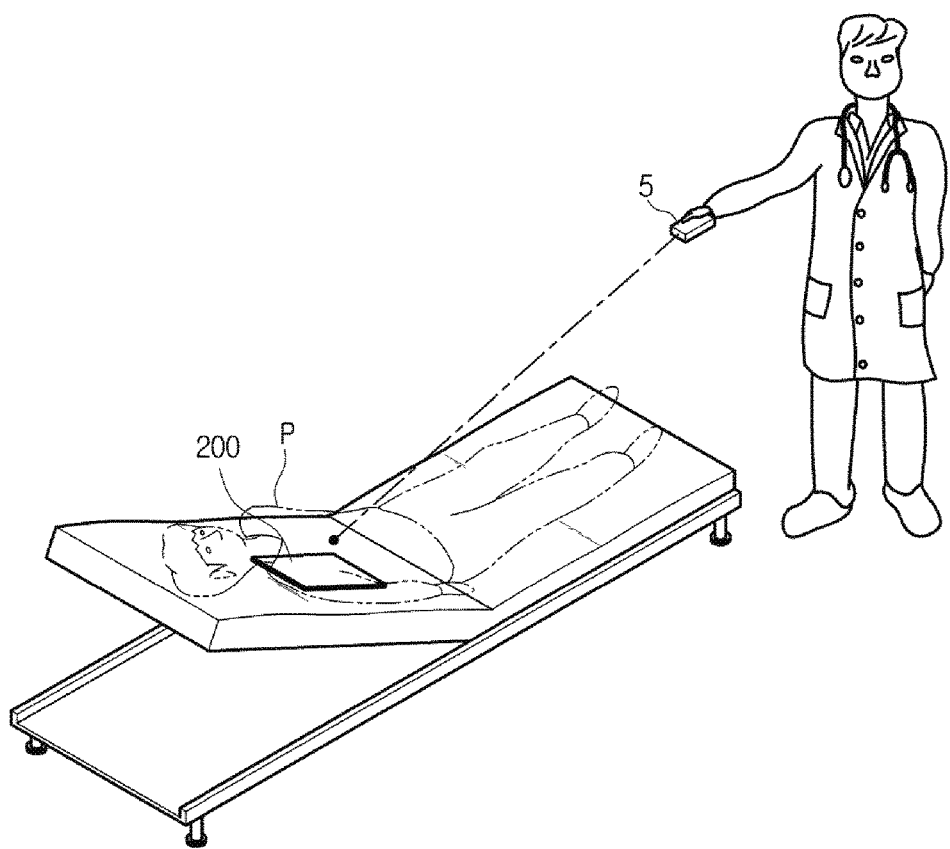
FIG. 6 illustrates an example in which a multi-marker array appears on a marker image.
Figure 7:
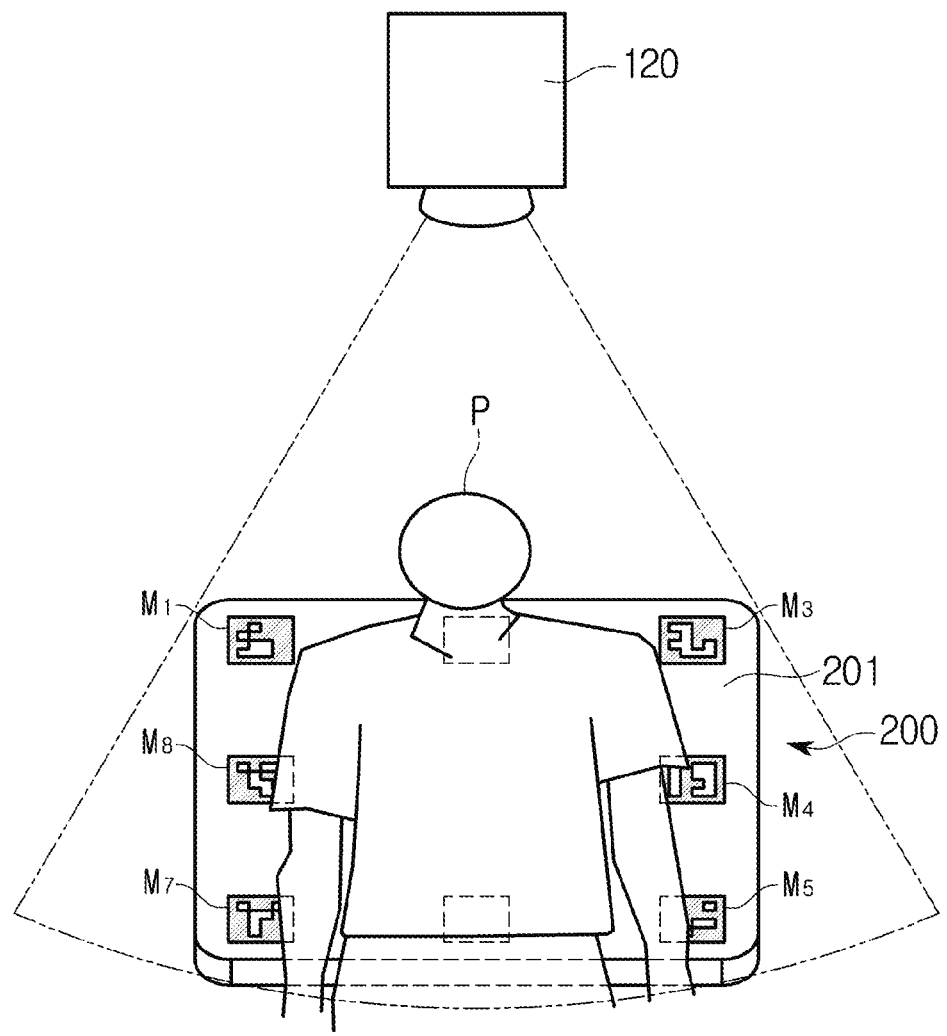
FIG. 7 illustrates an example of a method of acquiring SOD.

FIG. 5A illustrates the internal structure of an X-ray detector, FIG. 5B illustrates an example of an X-ray detector on which a multi-marker array is disposed, FIG. 6 shows an example in which a multi-marker array appears on a marker image, and FIG. 7 is a view for describing an example of a method of acquiring SOD.

Referring to FIGS. 5A and 5B, the X-ray detector 200 may include an X-ray sensor to detect X-rays and to generate and read out electrical signals corresponding to the detected X-rays, and a case which forms the outer appearance of the X-ray detector 200 and in which the X-ray sensor is installed.

As shown in FIG. 5A, the X-ray detector 200 may include a light receptor 210 to detect X-rays and convert the X-rays into electrical signals, and a read-out circuit 220 to read out the electrical signals.

The light receptor 210 may be made of a single crystal semiconductor material in order to ensure high resolution, high response speed, and a high dynamic region even under conditions of low energy and a small dose of X-rays. The single crystal semiconductor material may be Ge, CdTe, CdZnTe, or GaAs.

The light receptor 210 may be in the form of a PIN photodiode. The PIN photodiode is fabricated by bonding a p-type semiconductor substrate 213 having a 2D array structure on the lower surface of a n-type semiconductor substrate 211 having high resistance.

The read-out circuit 220, which is fabricated according to a CMOS process, may form a 2D array structure to be coupled with the p-type semiconductor substrate 213 of the light receptor 210 in units of pixels. The read-out circuit 220 and the light receptor 210 may be coupled by a Flip-Chip Bonding (FCB) method. More specifically, the read-out circuit 220 and the light receptor 210 may be coupled by forming bumps 230 with Pb Sn, In, or the like, reflowing, applying heat, and then compressing. However, the structure of the X-ray sensor shown in FIG. 5A is an example that can be applied to the X-ray detector 200, and the X-ray detector 200 may adopt an X-ray sensor having any other structure.

The X-ray detector 200 may be sold together with the X-ray imaging apparatus 100, or may be sold separately from the X-ray imaging apparatus 100, registered in the X-ray imaging apparatus 100, and then used. Accordingly, the X-ray imaging apparatus 100 may or may not include the X-ray detector 200.

Referring to FIG. 5B, a multi-marker array including a plurality of markers $M_1$, $M_2$, $M_3$, $M_4$, $M_5$, $M_6$, $M_7$, and $M_8$ may be disposed on a surface of the X-ray detector 200. The multi-marker array may be printed or attached on the surface of the X-ray detector 200, or engraved or embossed in the surface of the X-ray detector 200. That is, the multi-marker array may be formed by any method as long as it can be optically identified on a marker image photographed by the photographing device 120.

The multi-marker array may be formed in the front surface of the X-ray detector 200, that is, in the surface of the X-ray detector 200 to which X-rays are incident. Also, since radiography is performed after an object is located on the front surface of the X-ray detector 200, more specifically, after the center of the X-ray detector 200 is located to correspond to a target part of an object to be scanned, the plurality of markers $M_1$, $M_2$, $M_3$, $M_4$, $M_5$, $M_6$, $M_7$, and $M_8$ may be located on the edges of the X-ray detector 200.

The plurality of markers $M_1$, $M_2$, $M_3$, $M_4$, $M_5$, $M_6$, $M_7$, and $M_8$ may be formed such that they can be identified from each other. For example, as shown in FIG. 5B, the individual markers $M_1$, $M_2$, $M_3$, $M_4$, $M_5$, $M_6$, $M_7$, and $M_8$ may have different patterns to be identified from each other. According to another example, the individual markers $M_1$, $M_2$, $M_3$, $M_4$, $M_5$, $M_6$, $M_7$, and $M_8$ may have different colors to be identified from each other.

In order for the user to be able to determine a pose of the X-ray detector 200 even when only one marker is detected from a marker image photographed by the photographing device 120, each of the markers $M_1$, $M_2$, $M_3$, $M_4$, $M_5$, $M_6$, $M_7$, and $M_8$ may have a predetermined area. For example, each marker may be in the shape of a quadrangle having four vertices, and the markers $M_1$, $M_2$, $M_3$, $M_4$, $M_5$, $M_6$, $M_7$, and $M_8$ may be distinguished from each other by different patterns formed in the insides of the quadrangles.

In the current embodiment, the shapes, patterns, colors, etc. of the markers $M_1$, $M_2$, $M_3$, $M_4$, $M_5$, $M_6$, $M_7$, and $M_8$ are not limited, as long as the markers $M_1$, $M_2$, $M_3$, $M_4$, $M_5$, $M_6$, $M_7$, and $M_8$ can be distinguished from each other, and each marker has a predetermined area so that the pose of the X-ray detector 200 can be determined even when only one marker is detected.

Also, in the example of FIG. 5B, eight markers of $M_1$, $M_2$, $M_3$, $M_4$, $M_5$, $M_6$, $M_7$, and $M_8$ are shown, however, the number of the markers is not limited. That is, an appropriate number of markers may be formed in consideration of the size of the X-ray detector 200, the positions of markers, etc.

For radiography, after an object is located on the front surface of the X-ray detector 200, a marker image may be photographed by the photographing device 120. At this time, at least one of the plurality of markers $M_1$, $M_2$, $M_3$, $M_4$, $M_5$, $M_6$, $M_7$, and $M_8$ may be not covered by the object to appear on the marker image, according to the location or size of the object, as shown in FIG. 6.

The controller 140 may receive the marker image photographed by the photographing device 120, and detect a marker from the received marker image. In order for the controller 140 to detect the marker, the features of the markers $M_1$, $M_2$, $M_3$, $M_4$, $M_5$, $M_6$, $M_7$, and $M_8$, such as the shapes, patterns, or colors of the markers $M_1$, $M_2$, $M_3$, $M_4$, $M_5$, $M_6$, $M_7$, and $M_8$, may be stored in advance in the storage 170, and the controller 140 may recognize the marker appearing on the marker image using one of various recognition algorithms.

For example, if each marker is in the shape of a quadrangle having four vertices, the controller 140 may detect four vertices from a marker image, and recognize a quadrangle formed by the detected vertices.

Also, the controller 140 may recognize a pattern or color in the quadrangle to determine which one of the plurality of markers $M_1$, $M_2$, $M_3$, $M_4$, $M_5$, $M_6$, $M_7$, and $M_8$ the corresponding marker corresponds to.

Also, the storage 170 may store information about the locations of the markers $M_1$, $M_2$, $M_3$, $M_4$, $M_5$, $M_6$, $M_7$, and $M_8$ in the X-ray detector 200. For example, information about distances of the respective markers $M_1$, $M_2$, $M_3$, $M_4$, $M_5$, $M_6$, $M_7$, and $M_8$ to the center of the X-ray detector 200, and information about directions of the respective markers $M_1$, $M_2$, $M_3$, $M_4$, $M_5$, $M_6$, $M_7$, and $M_8$ with respect to the center of the X-ray detector 200 may be stored in the storage 170. For example, the information may be stored in the form of 2D spatial coordinates.

The controller 140 may apply a pose estimation algorithm and a camera calibration parameter using the marker to calculate a transition matrix between the detected marker and the photographing device 120, and to acquire the center location and pose of the marker on the coordinate system of the camera with respect to the photographing device 120.

Then, the controller 140 may calculate a center location of the X-ray detector 200 using a geometrical relationship between the detected marker and the center of the X-ray detector 200. Then, the controller 140 may acquire SID which is the distance between the X-ray source 110 and the X-ray detector 200, based on the calculated transition matrix and the center location of the X-ray detector 200.

The controller 140 may subtract SOD from the SID to decide a thickness of the object. The SOD may be acquired by various methods. For example, the SOD may be measured, or may be acquired by locating a separate marker on the object as shown in FIG. 7, photographing the object through the photographing device 120 to acquire an object image, and then detecting the marker from the object image through the controller 140. Herein, the separate marker may be spotlight SL irradiated from a light source such as laser. However, in the current embodiment, a method of acquiring the SOD is not limited.

Figure 8:
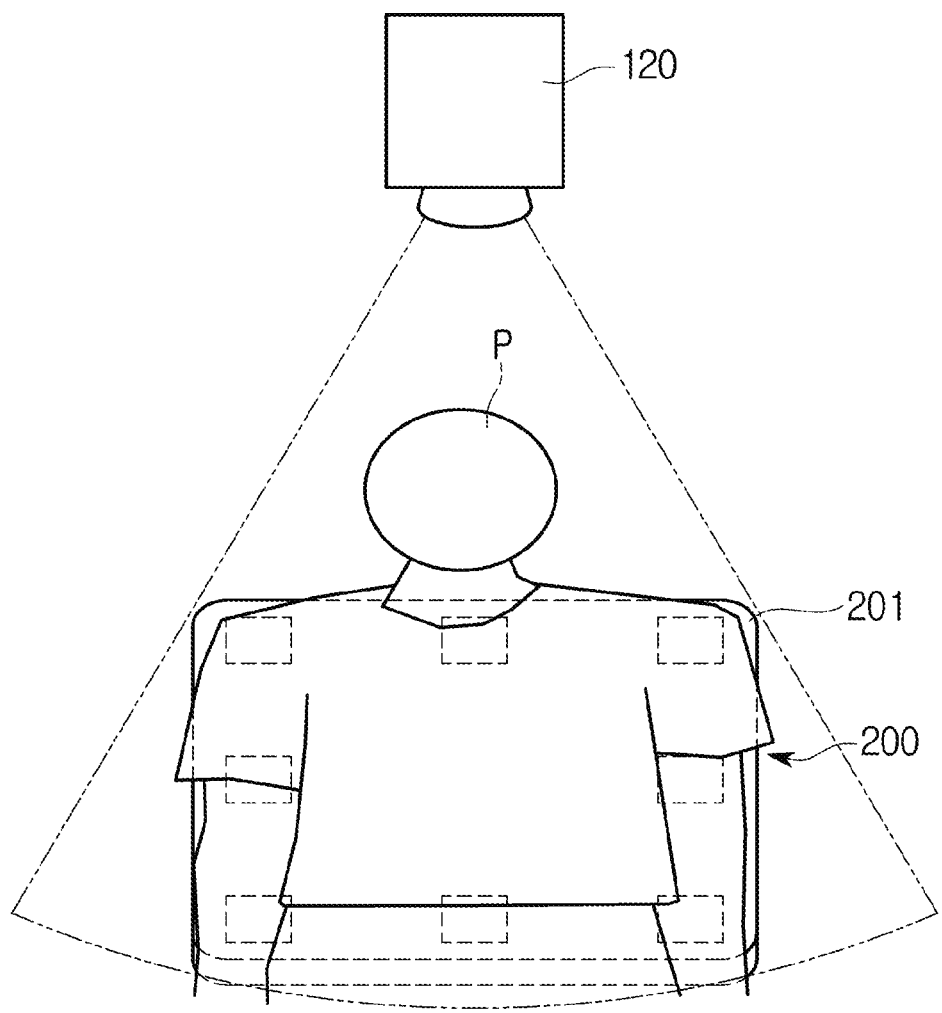
FIG. 8 illustrates an example of a case in which no multi-marker array appears on a marker image.

FIG. 8 illustrates an example of a case in which no multi-marker array appears on a marker image.

There may be a case in which all of the plurality of markers $M_1$, $M_2$, $M_3$, $M_4$, $M_5$, $M_6$, $M_7$, and $M_8$ are covered by an object according to the size and position of the object, as shown in FIG. 8. In this case, no marker may be detected from a marker image.

As such, if no marker is detected from the marker image, the controller 140 may output a notice for a user. For example, the controller 140 may output a notice visually through the display 151 of the workstation 150 or through the display provided in the sub user interface 80. Also, the controller 140 may output a notice aurally through a speaker provided in the workstation 150 or the sub user interface 80, or the controller 140 may output a notice visually or aurally through a mobile device which the user possesses.

Figure 9:
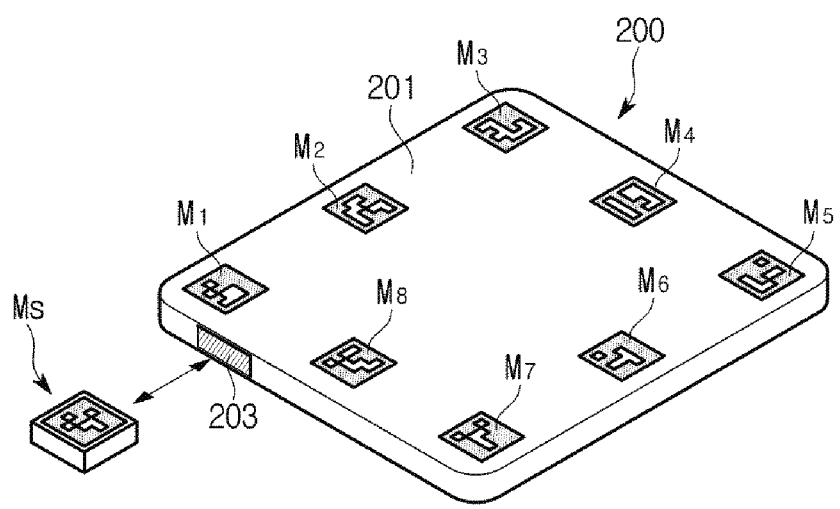
FIGS. 9, 10, and 11 illustrate examples of a single marker that is installed in an X-ray detector.
Figure 10:
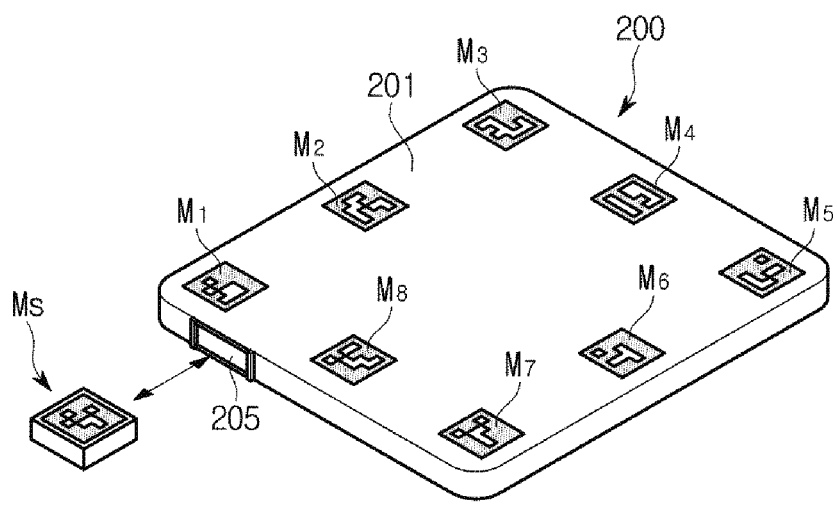
Figure 11:
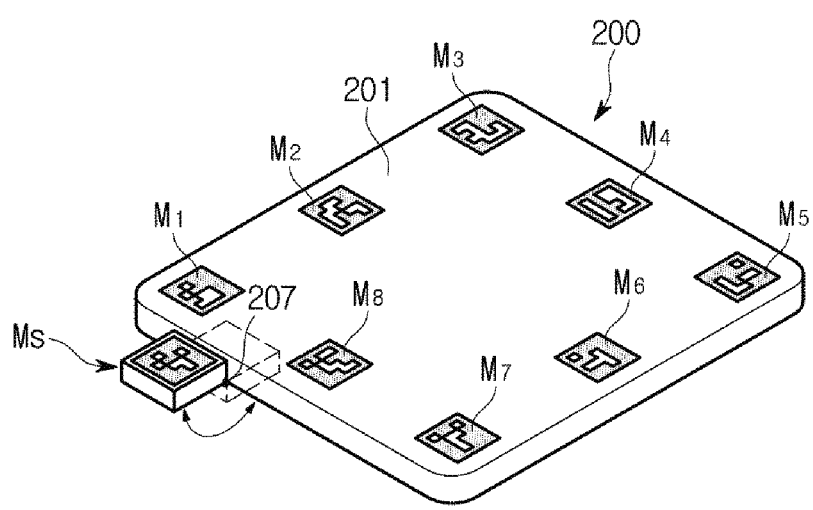

FIGS. 9, 10, and 11 illustrate examples of a single marker that is installed in an X-ray detector.

If all of the plurality of markers $M_1$, $M_2$, $M_3$, $M_4$, $M_5$, $M_6$, $M_7$, $M_8$ formed in the surface of the X-ray detector 200 are covered by an object, as described above, a separate single marker may be used.

As shown in FIGS. 9, 10, and 11, a separate single marker Ms may also have a shape, a pattern, or a color that can be identified from a marker image, and may have features distinguished from those of the multi-marker array provided in the front surface of the X-ray detector 200.

The single marker Ms may be detachably attached to the X-ray detector 200. For example, as shown in FIG. 9, the single marker Ms may be attached to the X-ray detector 200 by an attraction force between a magnet included in the single marker Ms and a magnet 203 included in the X-ray detector 200.

As another example, as shown in FIG. 10, the single marker Ms may be attached to the X-ray detector 200 by forming a holder 205 in one lateral surface of the X-ray detector 200 and mechanically coupling the single marker Ms with the holder 205.

As still another example, as shown in FIG. 11, the single marker Ms may be coupled with the X-ray detector 200 using a structure such as a hinge 207. The single marker Ms may be folded to be located on the rear surface of the X-ray detector 200 before a notice informing that no marker is detected is output. If a notice informing that no marker is detected is output, the user may unfold the folded single marker Ms such that the single marker Ms can appear on the same plane as the X-ray detector 200.

The magnet 203, the holder 205, or the structure such as the hinge 207, provided for attaching the single marker Ms to the X-ray detector 200, may be formed in any one of the lateral surfaces of the X-ray detector 200. If the magnet 203, the holder 205, or the structure such as the hinge 207 is formed in one lateral surface of the X-ray detector 200, corresponding to a patient's thickness direction not the patient's longitudinal direction, as shown in FIGS. 9, 10, and 11, probability that the single marker MS will be covered by the patient P may be reduced. Herein, the lateral surface of the X-ray detector 200 may include all of the remaining surfaces except for the front surface to which X-rays are incident and the rear surface that is opposite to the front surface.

If no single marker Ms is attached to the X-ray detector 200, the user may locate the single marker Ms adjacent to the X-ray detector 200.

When the single marker Ms is used, likewise, a marker image captured by the photographing device 120 may be transferred to the controller 140, and the controller 140 may analyze the marker image to detect the single marker Ms. Details about operation of detecting the single marker Ms and determining the location and pose of the X-ray detector 200 using the single marker Ms have been described above in the example in which the multi-marker array is used. Also, the storage 170 may store the features of the single marker Ms or a location relationship of the single marker Ms with respect to the center of the X-ray detector 200, in addition to the features of the markers constituting the multi-marker array. The controller 140 may use the features of the single marker Ms stored in the storage 170 to detect the single marker Ms, and use the location relationship of the single marker Ms with respect to the center of the X-ray detector 200 to determine SID or a location of the X-ray detector 200.

Figure 12:
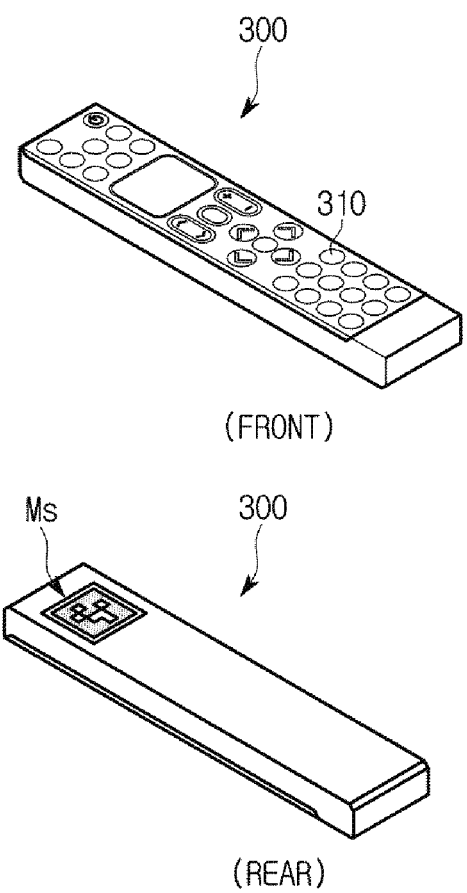
FIGS. 12 and 13 illustrate an example in which a remote controller is used as a single marker.
Figure 13:
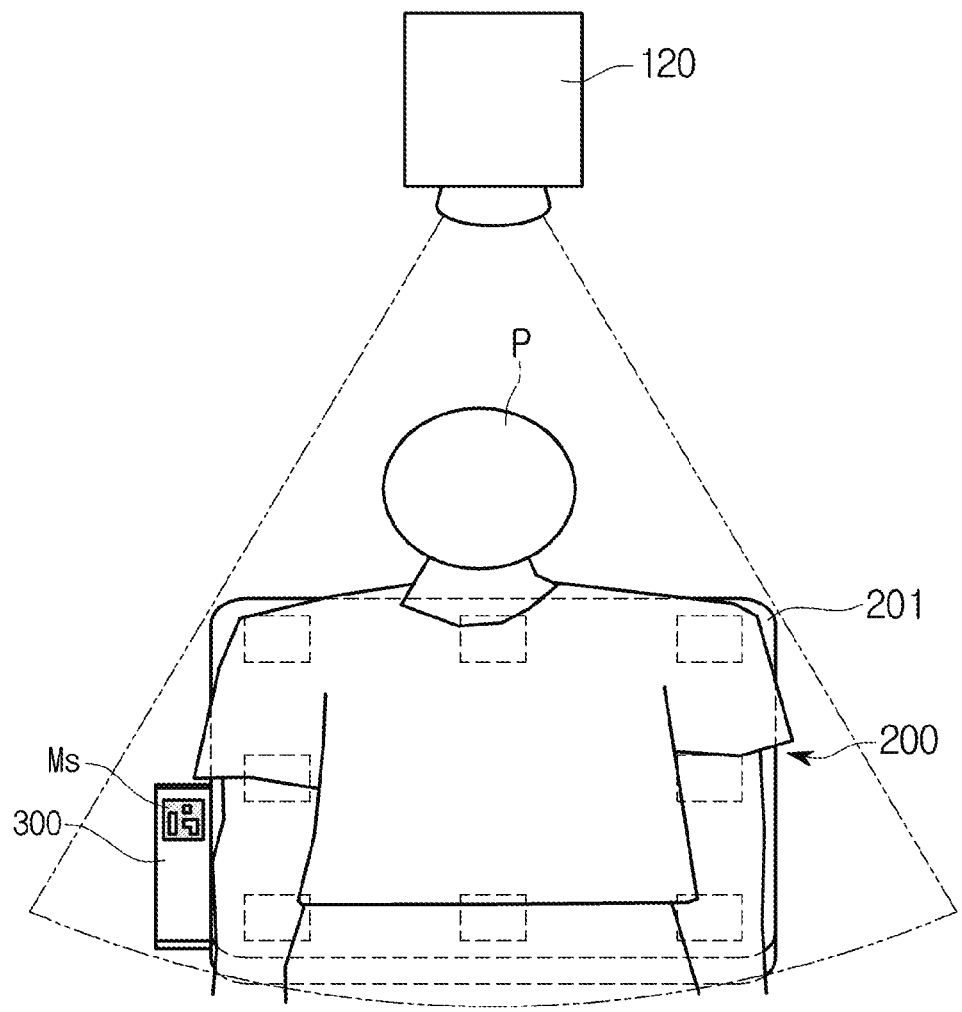

FIGS. 12 and 13 illustrate an example in which a remote controller is used as a single marker.

Referring to FIG. 12, the X-ray imaging apparatus 100 may further include a remote controller 300 for receiving a user's control command remotely, in addition to the workstation 150 or the sub user interface 80.

The user may manipulate an inputter 310 provided in the remote controller 300 to input various control commands related to irradiation of X-rays, movement of the X-ray source 110, photographing of the photographing device 120, etc.

Also, as shown in FIG. 12, a single marker Ms may be formed in the rear surface of the remote controller 300. As described above, if the controller 140 fails to detect at least one of the plurality of markers constituting the multi-marker array so that a notice is output, the user may locate the remote controller 300 next to the X-ray detector 200, as shown in FIG. 13.

At this time, the user may locate the remote controller 300 such that the rear surface of the remote controller 300 faces the photographing device 120, so that the single marker Ms can appear on a marker image. Also, the user may locate the remote controller 300 horizontally on the same plane as the X-ray detector 200 such that the pose of the X-ray detector 200 can be estimated from the pose of the single marker Ms.

In this case, a marker image may be photographed when no motion is detected from moving images for a predetermined time period, or when a predetermined time period elapses after a scanning command is input through the inputter 310 provided in the remote controller 300, as described above.

Figure 14:
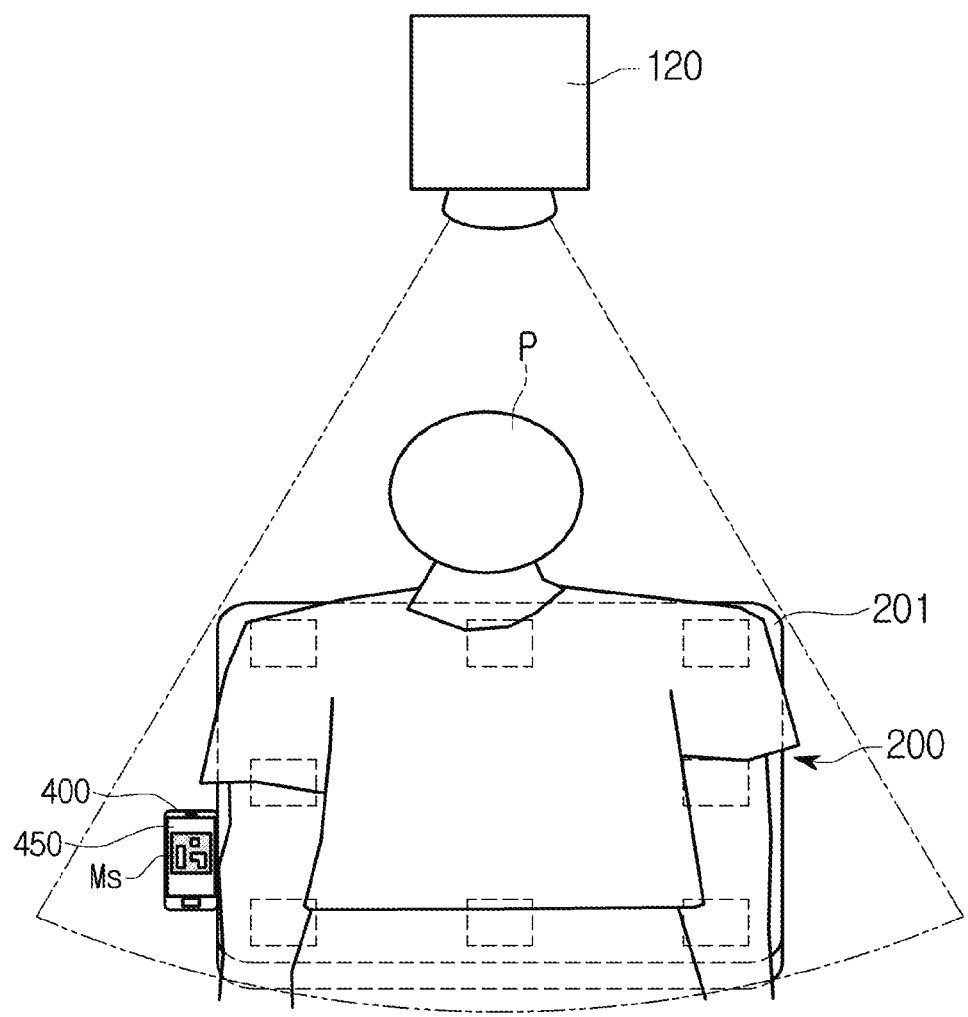
FIG. 14 illustrates an example in which a mobile device is used as a single marker.

FIG. 14 illustrates an example in which a mobile device is used as a single marker.

As another example, a mobile device 400, such as a smart phone, a smart watch, a tablet PC, etc., may be used as a single marker. If the mobile device 400 is a smart phone, a display 450 of the mobile device 400 may display a single marker Ms, as shown in FIG. 14.

According to an example for displaying the single marker Ms on the display 450, an application installed in the mobile device 400 may be executed. The application may have been installed in the mobile device 400 when the mobile device 400 was manufactured, or may have been downloaded from an external server by the user.

If the controller 140 fails to detect at least one of the plurality of markers constituting the multi-marker array so that a notice informing that no marker is detected is output, the user may execute the application for displaying the single marker Ms, and then locate the mobile device 400 on which the single marker Ms is displayed, next to the X-ray detector 200. At this time, the user may locate the mobile device 400 such that the display 450 of the mobile device 400 faces the photographing device 120 so that the single marker Ms can appear on a marker image.

If the mobile device 400 is used as the single marker Ms, pose information measured by a pose sensor such as a gyro sensor installed in the mobile device 400 may be used to determine a pose of the X-ray detector 200. For this, if the application for displaying the single marker Ms is executed, the mobile device 400 may communicate with the communicator 180 to transmit and receive data.

If the mobile device 400 is connected to the communicator 180, the mobile device 400 may transmit pose information, such as a roll, a pitch, a yaw, etc., measured by itself, to the communicator 180. The controller 140 may minimize an error of a pose information determination value of the X-ray detector 200, using the pose information received from the mobile device 400.

Also, a marker image may be photographed according to one of the above-described examples. Alternatively, the controller 140 may detect motion of the mobile device 400 based on acceleration or pose information of the mobile device 400 received from an accelerometer or a pose sensor of the mobile device 400, and transmit a control signal to the photographing device 120 if no motion of the mobile device 400 is detected for a predetermined time period to thus capture a marker image through the photographing device 120.

Figure 15:
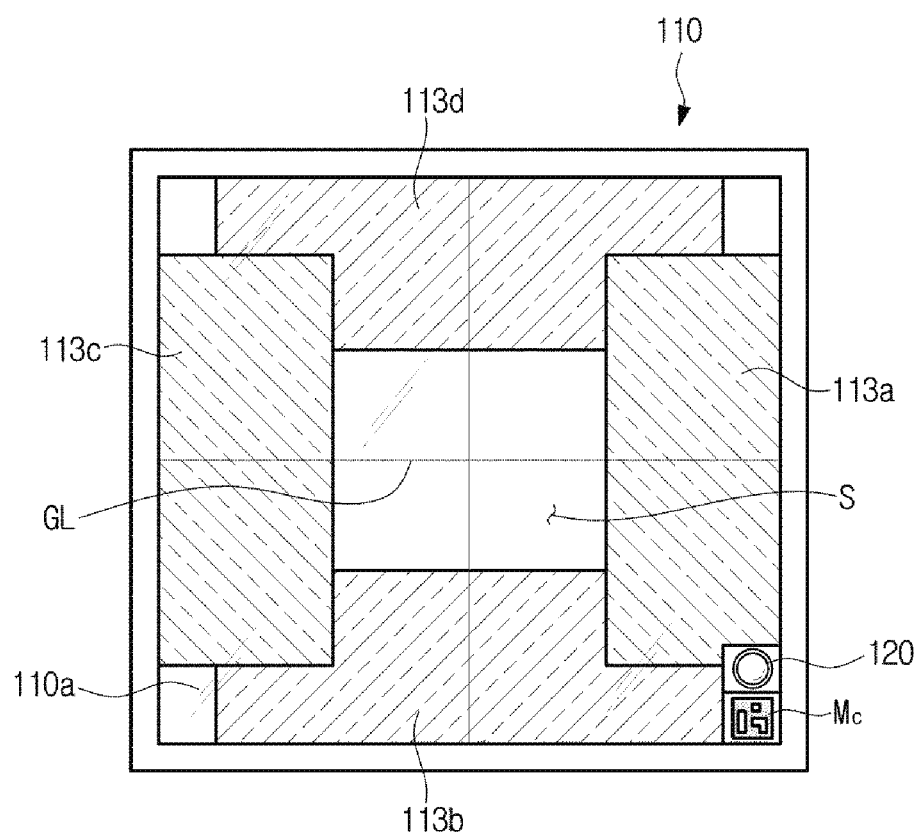
FIG. 15 illustrates an example of a marker formed in an X-ray source.

FIG. 15 illustrates an example of a marker formed in an X-ray source.

Contrary to the above-described examples, a collimator marker Mc may be formed in the X-ray source 110, and the collimator marker Mc may be photographed by a camera provided in the mobile device 400.

If the controller 140 fails to detect at least one of the plurality of markers constituting the multi-marker array so that a notice is output, a user may execute an application on the mobile device 400, and then locate the mobile device 400 next to the X-ray detector 200. The executed application may include operation of photographing the collimator marker Mc with the camera to acquire a marker image and then transmitting the marker image to the communicator 180.

The controller 140 may analyze the marker image received by the communicator 180 to detect the collimator marker Mc, and determine a pose of the X-ray detector 200 and SID, based on a location and pose of the collimator marker Mc.

Alternatively, as described above in the example of FIG. 14, the application executed by the mobile device 400 may further include operation of displaying a single marker Ms. In this case, the camera of the mobile device 400 may photograph the collimator marker Mc of the X-ray source 110, and the photographing device 120 may photograph the single marker Ms displayed on the display 450 of the mobile device 400.

The photographed images may be transmitted to the controller 140, and the controller 140 may determine a relative location and pose of the X-ray detector 200 with respect to the X-ray source 110, and a relative location and pose of the X-ray source 110 with respect to the X-ray detector 200, thereby improving the accuracy of result values.

In both of the case of detecting at least one of the plurality of markers included in the multi-marker array and the case of detecting the single marker Ms, the controller 140 may determine SID based on the location of the detected marker, and determine a thickness of the object based on the SID. As described above, the controller 140 may set an X-ray irradiation condition based on the thickness of the object, and control the X-ray source 110 to perform radiography according to the X-ray irradiation condition.

In order to control the X-ray source 110, the controller 140 may itself not necessarily transmit a control signal for controlling the X-ray source 110 to the X-ray source 110. For example, the controller 140 may control the X-ray source 110 through another component such as a high-voltage generator.

Also, in the automatic move mode, the controller 140 may automatically align the X-ray source 110 based on the location or pose of the X-ray detector 200. For this, the controller 140 may calculate a movement direction and a movement amount of the X-ray source 110, and transmit a control signal corresponding to the movement direction and the movement amount of the X-ray source 110 to the source driver 130, and the source driver 130 may move the X-ray source 110 according to the control signal to thereby align the location or pose of the X-ray source 110 in correspondence to the X-ray detector 200.

Hereinafter, an embodiment of a method of controlling an X-ray imaging apparatus according to an aspect will be described. In the method of controlling the X-ray imaging apparatus, the X-ray imaging apparatus may be the X-ray imaging apparatus 100 described above. Accordingly, the above descriptions with reference to FIGS. 1 to 15 can be applied in the same way to the method of controlling the X-ray imaging apparatus.

Figure 16:
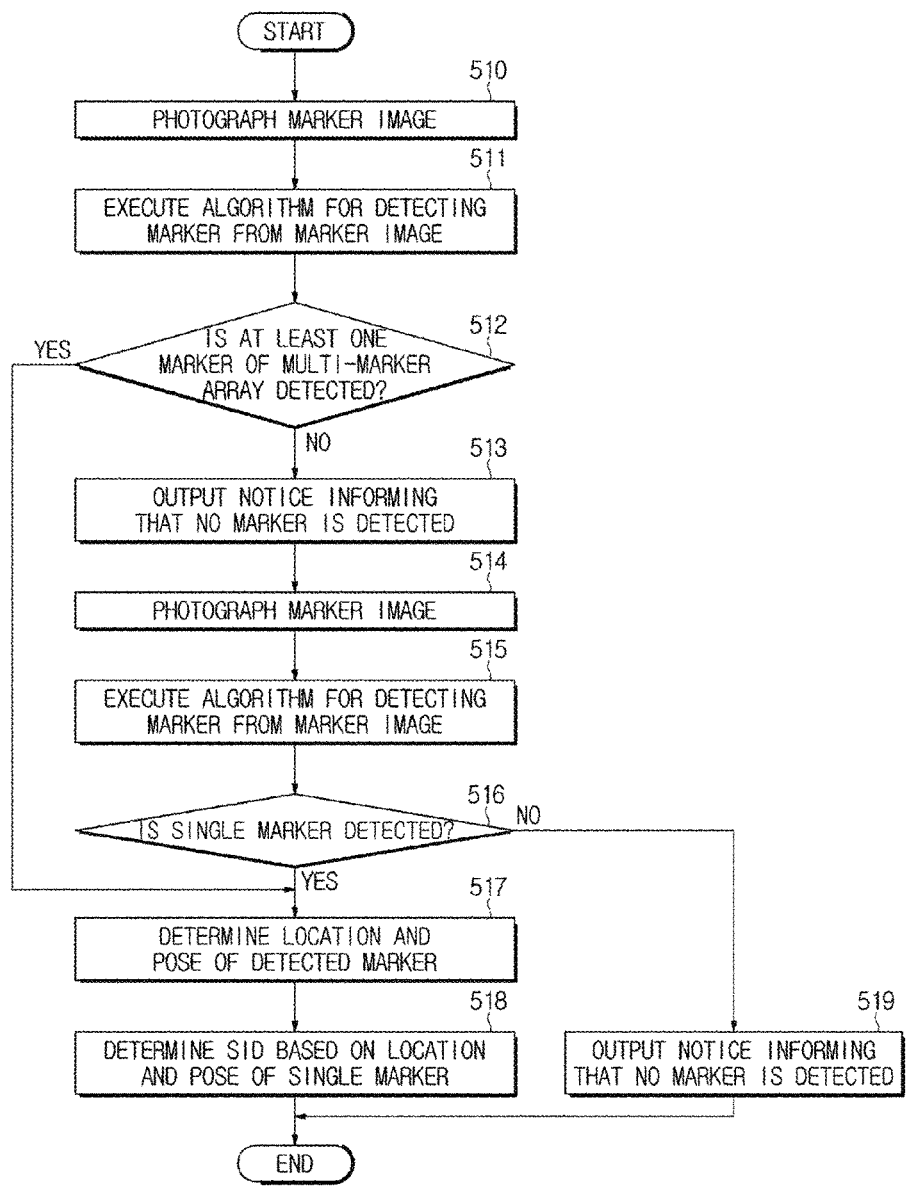
FIGS. 16, 17, and 18 illustrate flowcharts of a method of controlling an X-ray imaging apparatus according to an embodiment of the present disclosure.
Figure 17:
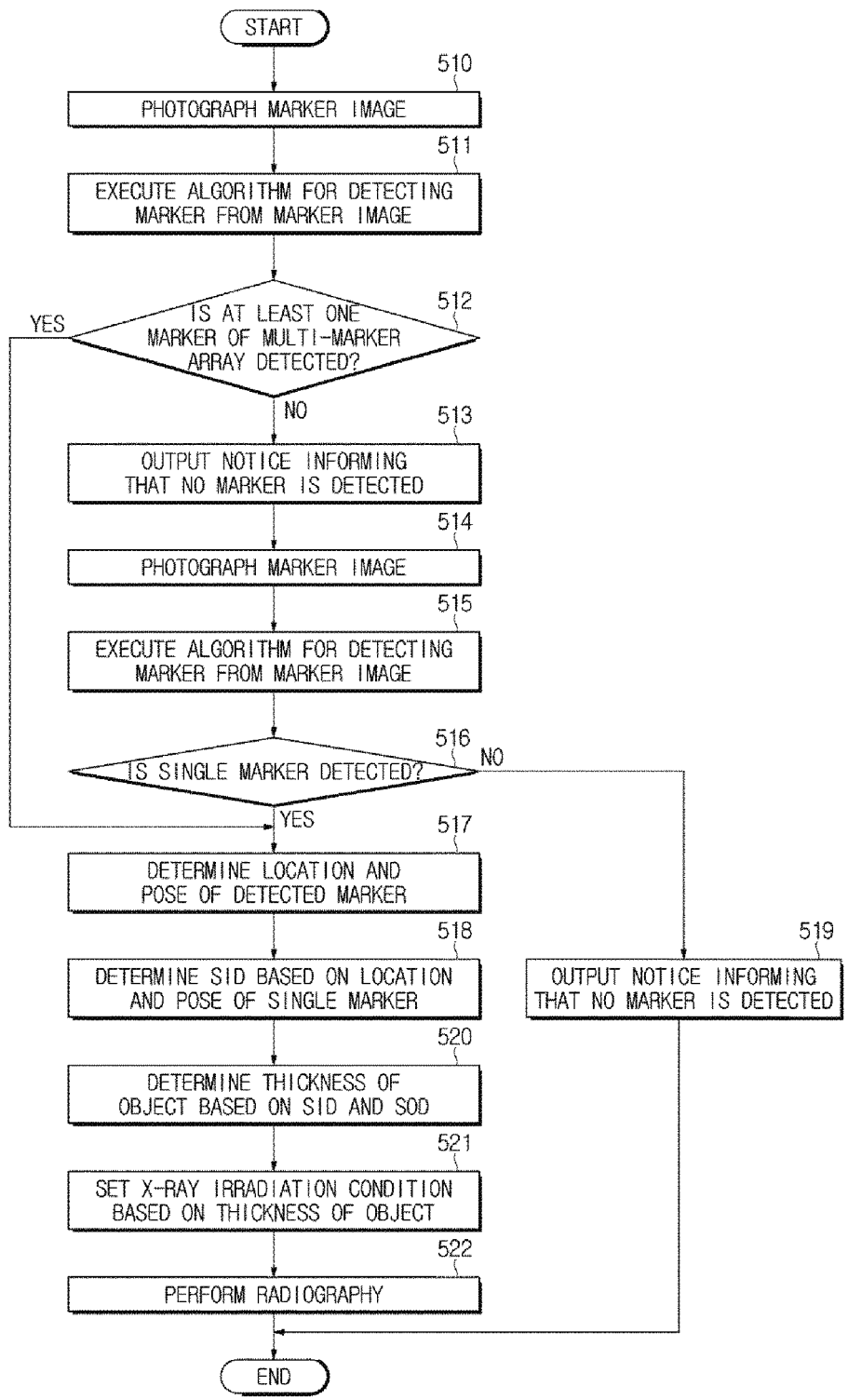
Figure 18:
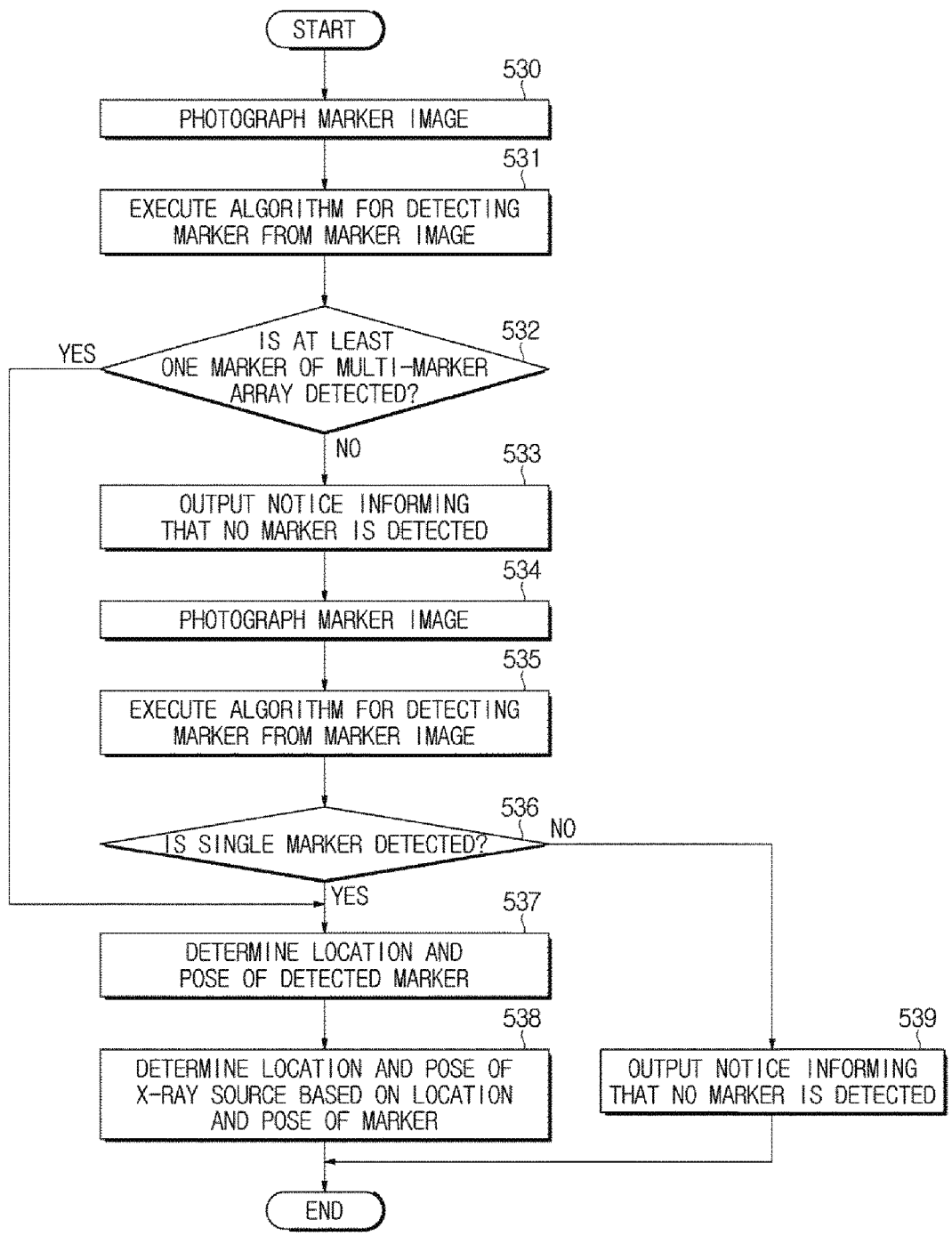

FIGS. 16, 17, and 18 illustrate flowcharts of a method of controlling an X-ray imaging apparatus according to an embodiment of the present disclosure.

Referring to FIG. 16, a marker image may be photographed, in operation 510. The photographing device 120 installed in the X-ray source 110 may photograph moving images, and if a predetermined event occurs, the photographing device 120 may capture a still image. The captured still image may be a marker image.

The predetermined event for capturing the still image may be a user's control command input through the inputter provided in the remote controller 300 (see FIG. 12), the workstation 150, or the sub user interface 80. The marker image may be captured when a control command is received, when a predetermined time period elapses after a control command is received, or periodically for a predetermined time period from when a control command is received.

Alternatively, the controller 140 may analyze moving images photographed by the photographing device 120 in real time to detect motion, and if the controller 140 detects no motion for a predetermined time period, the controller 140 may determine that it is ready to perform radiography, and capture a marker image.

Then, an algorithm for detecting a marker from the marker image may be executed, in operation 511. For example, if the marker is in the shape of a quadrangle formed by four vertices, four vertices may be detected from the marker image, and a quadrangle formed by the detected vertices may be recognized.

However, there may be a case in which all of a plurality of markers are covered by an object P according to the location or size of the object P. That is, if none of a plurality of markers included in a multi-marker array is detected ("No" in operation 512), a notice informing that no marker is detected may be output, in operation 513. The notice informing that no marker is detected may be output visually or aurally.

If a notice informing that no marker is detected is output, a user may use a single marker Ms. For example, the single marker Ms may be detachably attached to the X-ray detector 200, or may be foldable to be located on the X-ray detector 200, as shown in FIGS. 9, 10, and 11. Or, the user may use a single marker Ms formed in the remote controller 300. Or, the user may execute an application installed in the mobile device 400 to display a single marker Ms on the display 450 of the mobile device 400. Any one of the above-described examples may be used as long as it can locate a single marker Ms horizontally on the same plane as the X-ray detector 200 so that the single marker Ms can appear on a marker image photographed by the photographing device 120.

Then, a marker image may be again photographed, in operation 514. As described above in operation 510, if a predetermined event occurs, a still image may be captured. Also, in the case in which the single marker Ms displayed on the mobile device 400 is photographed, an application for displaying the single marker Ms may be executed, and then a marker image may be captured if no motion is detected by an accelerometer or a pose sensor provided in the mobile device 400 for a predetermined time period.

Thereafter, an algorithm for detecting the single marker Ms from the marker image may be executed, in operation 515. At this time, the single marker Ms may be detected based on the features of single markers stored in the storage 170.

If the single marker Ms is detected ("Yes" in operation 516), a location and pose of the single marker Ms may be determined, in operation 517, and SID may be determined based on the location and pose of the single marker Ms, in operation 518. Details about operation of determining the location and pose of the single marker Ms and the SID have been described above in the embodiment of the X-ray imaging apparatus 100, and accordingly further descriptions thereof will be omitted.

Meanwhile, if no single marker Ms is detected ("No" in operation 516), a notice informing that no marker is detected may be output, in operation 519.

Also, if at least one marker of the plurality of markers included in the multi-marker array is detected ("Yes" in operation 512), likewise, a location and pose of the detected marker may be determined, in operation 517, and SID may be determined based on the location and pose of the marker, in operation 518.

Referring to FIG. 17, the thickness of the object may be determined based on the determined SID and SOD, in operation 520. The SOD may be acquired by various methods, and in the current embodiment, a method of acquiring SOD is not limited.

Then, an X-ray irradiation condition may be set based on the thickness of the object, in operation 521. The X-ray irradiation condition may include at least one of a tub voltage, tube current, an exposure time, the kind and thickness of a filter, a target material of an anode, an exposure parameter such as a focal spot size, the angle or center position of a grid, and a scattering parameter such as Field Of View (FOV).

If the X-ray irradiation condition is set, the controller 140 may control the X-ray source 110 to irradiate X-rays according to the X-ray irradiation condition to thereby perform radiography, in operation 522.

Meanwhile, the location and pose of the X-ray source 110 may be aligned using the marker. Referring to FIG. 18, a series of operations from operation 530 of photographing a marker image to operation 536 of detecting a single marker Ms are the same as the series of operations from operation 510 of photographing the marker image to operation 516 of detecting the single marker Ms, as described above with reference to FIG. 16.

If at least one marker included in a multi-marker array is detected ("Yes" in operation 532), or if a single marker Ms is detected in operation 536, a location and pose of the detected marker may be determined, in operation 537. Then, the location and pose of the X-ray source 110 may be aligned based on the location and pose of the marker, in operation 538. That is, the location of the X-ray source 110 may be aligned to correspond to the determined location of the marker, and the pose of the X-ray source 110 may be aligned to correspond to the determined pose of the marker. In order to align the location or pose of the X-ray source 110, the controller 140 may calculate a movement direction and a movement amount of the X-ray source 110 to transmit a control signal corresponding to the movement direction and the movement amount of the X-ray source 110 to the source driver 130, and the source driver 130 may move the X-ray source 110 according to the control signal.

In the current example, likewise, if no single marker Ms is detected ("No" in operation 536), a notice informing that no marker is detected may be output, in operation 539.

Meanwhile, when the location and pose of the X-ray source 110 are aligned using the marker, SID may be calculated, like the above-described example.

A part of operations of the X-ray imaging apparatus and the control method thereof as described above may be stored as a program in computer-readable recording medium. The recording medium may be magnetic recording medium, such as Read Only Memory (ROM), a floppy disc, a hard disc, and the like, or optical recording medium, such as Compact Disc Read-Only Memory (CD-ROM), Digital Video Disc (DVD), and the like. However, the kind of the recording medium is not limited to these.

The recording medium may be included in a server providing applications or programs. The workstation 150, the sub user interface 80, or the mobile device 400 may be connected to the server to download the corresponding program.

For example, a program including operations of the controller 140 may be installed in the mobile device 400 so that the mobile device 400 performs the corresponding operations. In this case, the mobile device 400 may perform overall control operations of the X-ray imaging apparatus 100, as well as operations of detecting a marker, calculating SID, and aligning the location and pose of the X-ray source 110.

In the X-ray imaging apparatus, the method of controlling the X-ray imaging apparatus, and the X-ray detector according to an aspect, by photographing a marker provided on the X-ray detector through a camera, accurate information about the distance between the X-ray source and the X-ray detector and about the pose of the X-ray detector may be acquired with low cost.

The aforementioned descriptions are only for illustrative purposes, and it will be apparent that those skilled in the art can make various modifications, changes, and substitutions thereto without changing the technical spirit and essential features of the present disclosure. Thus, it should be understood that the exemplary embodiments and the accompanying drawings described above are merely for illustrative purposes and not for limitation purposes in all aspects. Although the present disclosure has been described with an exemplary embodiment, various changes and modifications may be suggested to one skilled in the art. It is intended that the present disclosure encompass such changes and modifications as fall within the scope of the appended claims.

What is claimed is:

1. An X-ray imaging apparatus comprising:
   an X-ray source configured to:
      generate X-rays; and
      irradiate the X-rays;
   a photographing device installed in the X-ray source, the photographing device is configured to photograph a marker image; and
   a controller configured to:
      output, when a marker of a plurality of markers constituting a multi-marker array formed in a surface of an X-ray detector is not detected from the marker image, a notice informing that the marker is not detected; and
      detect a single marker from another marker image photographed after the notice informing that the marker is not detected is outputted.

2. The X-ray imaging apparatus according to claim 1, wherein when at least one marker of the plurality of markers is detected, the controller is configured to:
   determine a location of the detected marker; and
   determine a Source to Image receptor Distance (SID) based on a location relationship between the detected marker and a center of the X-ray detector.

3. The X-ray imaging apparatus according to claim 2, wherein the controller is configured to:
   determine a location of the X-ray detector based on a location of the detected marker; and
   align a location of the X-ray source based on the location of the X-ray detector.

4. The X-ray imaging apparatus according to claim 2, wherein the controller is configured to:
   determine a thickness of an object based on the SID; and
   set an X-ray irradiation condition based on the thickness of the object.

5. The X-ray imaging apparatus according to claim 1, wherein when the single marker is detected, the controller is configured to:
   determine a location of the detected single marker; and
   determine an SID based on a location relationship between the detected single marker and a center of the X-ray detector.

6. The X-ray imaging apparatus according to claim 1, further comprising a storage configured to store features of the plurality of markers constituting the multi-marker array and features of the single marker.

7. The X-ray imaging apparatus according to claim 1, wherein the photographing device is configured to photograph a moving image, and
   wherein the controller is configured to detect motion from the moving image, and when the controller fails to detect motion from the moving image for a predetermined time period, the controller is configured to control the photographing device to photograph the marker image.

8. The X-ray imaging apparatus according to claim 1, wherein the single marker is displayed on a display of a mobile device, and
   wherein the X-ray imaging apparatus further comprising a communicator configured to receive at least one of acceleration information or pose information of the mobile device from the mobile device.

9. The X-ray imaging apparatus according to claim 8, wherein the controller is configured to:
   detect motion of the mobile device based on at least one of the acceleration information or the pose information of the mobile device; and
   transmit a control signal for causing the photographing device to photograph the other marker image to the photographing device when the controller fails to detect motion of the mobile device for a predetermined time period.

10. The X-ray imaging apparatus according to claim 8, wherein a collimator marker is formed in the X-ray source, and
    wherein the communicator is configured to receive a photographed image of the collimator marker from the mobile device.

11. The X-ray imaging apparatus according to claim 10, wherein the controller is configured to:
    determine a location of the X-ray source based on the photographed image of the collimator marker; and
    determine a location of the X-ray detector based on the marker image.

12. The X-ray imaging apparatus according to claim 1, wherein when at least one marker of the plurality of markers is detected or when the single marker is detected, the controller is configured to determine a pose of the X-ray detector based on the detected marker.

13. The X-ray imaging apparatus according to claim 12, wherein the controller is configured to align a pose of the X-ray source based on the pose of the X-ray detector.

14. An X-ray detector comprising:
    an X-ray sensor configured to:
       detect X-rays; and
       generate an electrical signal corresponding to the detected X-rays;
    a case configured to accommodate the X-ray sensor;
    a multi-marker array including a plurality of markers formed in a front surface of the case to which the X-rays are incident;
    a marker installation unit formed in one lateral surface of the case; and
    a single marker attached to the marker installation unit.

15. The X-ray detector according to claim 14, wherein the single marker may transition between a folded state and unfolded state with respect to the marker installation unit, and
    wherein the single marker is located on a rear surface of the X-ray detector when the single marker is folded and located on one lateral surface of the X-ray detector when the single marker is unfolded.

16. A method of controlling an X-ray imaging apparatus, the method comprising:
   photographing a marker image with a camera installed in an X-ray source;
   outputting, when a marker from a plurality of markers constituting a multi-marker array formed in a surface of an X-ray detector is not detected from the marker image, a notice informing that the marker is not detected; and
   detecting a single marker from another marker image photographed after the notice informing that the marker is not detected is outputted.

17. The method according to claim 16, further comprising:
   determining, when the single marker is detected, a location of the single marker; and
   determining a Source to Image receptor Distance (SID) based on a location relationship between the single marker and a center of the X-ray detector.

18. The method according to claim 16, wherein the photographing of the marker image comprises:
   detecting motion from a moving image photographed by the camera; and
   capturing the marker image when motion is not detected in the moving image for a predetermined time period.

19. The method according to claim 16, wherein the single marker is displayed on a display of a mobile device, and
   wherein the method further comprising receiving at least one of acceleration information or pose information of the mobile device from the mobile device.

20. The method according to claim 19, wherein the photographing of the marker image comprises:
   detecting motion of the mobile device based on at least one of the acceleration information or the pose information of the mobile device; and
   capturing another marker image when motion of the mobile device is not detected for a predetermined time period.

* * * * *